(12) United States Patent
Receveur et al.

(10) Patent No.: US 9,295,390 B2
(45) Date of Patent: Mar. 29, 2016

(54) FACIAL RECOGNITION BASED MONITORING SYSTEMS AND METHODS

(75) Inventors: Timothy J. Receveur, Guilford, IN (US); Michael P. Bish, Lawrenceburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 227 days.

(21) Appl. No.: 13/410,421

(22) Filed: Mar. 2, 2012

(65) Prior Publication Data

US 2013/0229283 A1 Sep. 5, 2013

(51) Int. Cl.
| | | |
|---|---|---|
| G08B 23/00 | (2006.01) | |
| A61B 5/00 | (2006.01) | |
| A61B 5/11 | (2006.01) | |

(52) U.S. Cl.
CPC .............. *A61B 5/002* (2013.01); *A61B 5/1113* (2013.01); *A61B 5/1128* (2013.01); *A61B 5/0022* (2013.01); *A61B 5/447* (2013.01)

(58) Field of Classification Search
None
See application file for complete search history.

(56) References Cited

U.S. PATENT DOCUMENTS

| | | |
|---|---|---|
| 1,388,242 A | 8/1921 | Dodds |
| 2,592,166 A | 4/1952 | McLean et al. |
| 2,604,639 A | 7/1952 | Killifer |
| 3,039,118 A | 6/1962 | Hutt |
| 3,919,727 A | 11/1975 | Paine |
| 3,972,320 A | 8/1976 | Kalman |
| 4,057,240 A | 11/1977 | Damico et al. |
| 4,087,872 A | 5/1978 | Smirle |
| 4,152,795 A | 5/1979 | Rodosta et al. |
| 4,196,425 A | 4/1980 | Williams, Jr. et al. |
| 4,539,560 A | 9/1985 | Fleck et al. |
| 4,633,237 A | 12/1986 | Tucknott et al. |
| 4,814,751 A | 3/1989 | Hawkins et al. |
| 4,837,877 A | 6/1989 | Hamada et al. |
| 4,907,845 A | 3/1990 | Wood |
| 4,947,152 A | 8/1990 | Hodges |
| 4,952,928 A | 8/1990 | Carroll et al. |
| 5,008,654 A | 4/1991 | Callaway |
| 5,095,560 A | 3/1992 | Volker |
| 5,107,845 A | 4/1992 | Guern et al. |
| 5,218,344 A | 6/1993 | Ricketts |
| 5,276,432 A | 1/1994 | Travis |
| 5,353,012 A | 10/1994 | Barham et al. |
| 5,365,217 A | 11/1994 | Toner |
| 5,416,695 A | 5/1995 | Stutman et al. |
| 5,490,298 A | 2/1996 | Goldsmith et al. |
| 5,495,288 A | 2/1996 | Broady et al. |
| 5,519,380 A | 5/1996 | Edwards |

(Continued)

FOREIGN PATENT DOCUMENTS

| | | |
|---|---|---|
| WO | WO 2006/011124 | 2/2006 |
| WO | WO 2006/117788 | 11/2006 |

OTHER PUBLICATIONS

U.S Appl. No. 13/305,884, Filed Nov. 29, 2011,, Confirmation #5382, Inventor-Irvin J. Vanderpohl.

*Primary Examiner* — Ojiako Nwugo
(74) *Attorney, Agent, or Firm* — Barnes & Thornburg LLP (57) ABSTRACT

A system to monitor patient position in bed and related methods of use are disclosed. The system to monitor patient position in bed relies on facial recognition and determination of the time spent by the patient in a particular position. Appropriate alarms and messages are displayed if the patient remains in a particular position for a time period greater than a predetermined threshold.

31 Claims, 6 Drawing Sheets

(56) References Cited

U.S. PATENT DOCUMENTS

| | | |
|---|---|---|
| 5,583,758 A | 12/1996 | McIlroy et al. |
| 5,633,627 A | 5/1997 | Newham |
| 5,650,770 A | 7/1997 | Schlager et al. |
| 5,714,931 A | 2/1998 | Petite et al. |
| 5,732,401 A | 3/1998 | Conway |
| 5,738,102 A | 4/1998 | Lemelson |
| 5,740,800 A | 4/1998 | Hendrickson et al. |
| 5,765,139 A | 6/1998 | Bondy |
| 5,780,798 A | 7/1998 | Hall-Jackson |
| 5,781,442 A | 7/1998 | Engleson et al. |
| 5,831,669 A | 11/1998 | Adrain |
| 5,844,488 A | 12/1998 | Musick |
| 5,877,675 A | 3/1999 | Rebstock et al. |
| 5,941,836 A | 8/1999 | Friedman |
| 5,946,659 A | 8/1999 | Lancelot et al. |
| 5,953,704 A | 9/1999 | McIlroy et al. |
| 6,049,281 A | 4/2000 | Osterweil |
| 6,067,019 A | 5/2000 | Scott |
| 6,078,261 A | 6/2000 | Davsko |
| 6,104,295 A | 8/2000 | Gaisser et al. |
| 6,125,350 A | 9/2000 | Dirbas |
| 6,154,139 A | 11/2000 | Heller |
| 6,160,478 A | 12/2000 | Jacobsen et al. |
| 6,169,484 B1 | 1/2001 | Schuchman et al. |
| 6,204,767 B1 | 3/2001 | Sparks |
| 6,259,355 B1 | 7/2001 | Chaco et al. |
| 6,402,691 B1 | 6/2002 | Peddicord et al. |
| 6,433,690 B2 | 8/2002 | Petelenz et al. |
| 6,466,125 B1 | 10/2002 | Richards et al. |
| 6,524,239 B1 | 2/2003 | Reed et al. |
| 6,583,727 B2 | 6/2003 | Nunome |
| 6,611,206 B2 | 8/2003 | Milanski et al. |
| 6,611,783 B2 | 8/2003 | Kelly, Jr. et al. |
| 6,624,754 B1 | 9/2003 | Hoffman et al. |
| 6,640,212 B1 | 10/2003 | Rosse |
| 6,674,403 B2 | 1/2004 | Gray et al. |
| 6,748,250 B1 | 6/2004 | Berman et al. |
| 6,753,783 B2 | 6/2004 | Friedman et al. |
| 6,788,206 B1 | 9/2004 | Edwards |
| 6,791,460 B2 | 9/2004 | Dixon et al. |
| 6,804,656 B1 | 10/2004 | Rosenfeld et al. |
| 6,821,258 B2 | 11/2004 | Reed et al. |
| 6,822,571 B2 | 11/2004 | Conway |
| 6,830,180 B2 | 12/2004 | Walsh |
| 6,838,992 B2 | 1/2005 | Tenarvitz |
| 6,876,303 B2 | 4/2005 | Reeder et al. |
| 6,897,781 B2 | 5/2005 | Cooper et al. |
| 6,900,732 B2 | 5/2005 | Richards |
| 6,909,367 B1 | 6/2005 | Wetmore |
| 6,915,170 B2 | 7/2005 | Engleson et al. |
| 6,941,239 B2 | 9/2005 | Unuma et al. |
| 6,958,706 B2 | 10/2005 | Chaco et al. |
| 6,968,294 B2 | 11/2005 | Gutta et al. |
| 6,975,230 B1 | 12/2005 | Brilman |
| 6,987,232 B2 | 1/2006 | Smith et al. |
| 7,001,334 B2 | 2/2006 | Reed et al. |
| 7,035,432 B2 | 4/2006 | Szuba |
| 7,110,569 B2 | 9/2006 | Brodsky et al. |
| 7,198,320 B2 | 4/2007 | Rasmussen |
| 7,242,306 B2 | 7/2007 | Wildman et al. |
| 7,369,680 B2 | 5/2008 | Trajkovic et al. |
| 7,406,731 B2 | 8/2008 | Menkedick et al. |
| 7,452,336 B2 | 11/2008 | Thompson |
| 7,502,498 B2 | 3/2009 | Wen et al. |
| 7,505,620 B2 | 3/2009 | Braune et al. |
| 7,987,069 B2 | 7/2011 | Rodgers et al. |
| 8,073,535 B2 | 12/2011 | Jung et al. |
| 2001/0044965 A1 | 11/2001 | Blevins |
| 2002/0046423 A1 | 4/2002 | Vilsmeier |
| 2002/0140559 A1 | 10/2002 | Zhou et al. |
| 2002/0165733 A1 | 11/2002 | Pulkkinen et al. |
| 2003/0013459 A1 | 1/2003 | Rankin et al. |
| 2003/0028399 A1 | 2/2003 | Davis et al. |
| 2003/0052971 A1* | 3/2003 | Gutta et al. .............. 348/159 |
| 2003/0058111 A1 | 3/2003 | Lee et al. |
| 2003/0069815 A1 | 4/2003 | Eisenberg et al. |
| 2003/0167187 A1 | 9/2003 | Bua |
| 2003/0169171 A1 | 9/2003 | Strubbe et al. |
| 2004/0172290 A1 | 9/2004 | Leven |
| 2004/0193449 A1 | 9/2004 | Wildman et al. |
| 2005/0125899 A1 | 6/2005 | Hanson et al. |
| 2005/0190062 A1 | 9/2005 | Sullivan et al. |
| 2005/0240086 A1 | 10/2005 | Akay |
| 2005/0242946 A1 | 11/2005 | Hubbard, Jr. et al. |
| 2005/0283382 A1 | 12/2005 | Donoghue et al. |
| 2006/0033625 A1 | 2/2006 | Johnson et al. |
| 2006/0053035 A1 | 3/2006 | Eisenberg |
| 2006/0056655 A1 | 3/2006 | Wen et al. |
| 2006/0265805 A1 | 11/2006 | Bellingroth |
| 2007/0033072 A1 | 2/2007 | Bildirici |
| 2007/0132597 A1* | 6/2007 | Rodgers ................. 340/573.1 |
| 2007/0157385 A1 | 7/2007 | Lemire et al. |
| 2007/0222599 A1 | 9/2007 | Coveley et al. |
| 2008/0021731 A1 | 1/2008 | Rodgers |
| 2008/0132808 A1* | 6/2008 | Lokhorst et al. ........... 600/595 |
| 2008/0250562 A1* | 10/2008 | Tekulve ..................... 5/613 |
| 2008/0272918 A1 | 11/2008 | Ingersoll |
| 2009/0044334 A1 | 2/2009 | Parsell et al. |
| 2009/0270770 A1* | 10/2009 | Petrosenko et al. ......... 600/595 |
| 2011/0301440 A1* | 12/2011 | Riley et al. ............... 600/301 |
| 2012/0026308 A1* | 2/2012 | Johnson et al. ............. 348/77 |
| 2012/0029879 A1 | 2/2012 | Sing et al. |
| 2012/0075464 A1* | 3/2012 | Derenne et al. ............ 348/135 |
| 2012/0161969 A1* | 6/2012 | Husen et al. ............. 340/573.1 |
| 2012/0323090 A1* | 12/2012 | Bechtel et al. ............ 600/306 |

* cited by examiner

FACIAL RECOGNITION BASED MONITORING SYSTEMS AND METHODS

BACKGROUND

Pressure sores are a significant concern for patients with reduced mobility in bed. Monitoring a patient to ensure that a patient has been re-positioned periodically is a challenging task and while various systems and methods exist for monitoring patient position in a bed, a need exists for continued development in this area.

BRIEF SUMMARY

The present disclosure includes one or more of the features recited in the appended claims and/or the following features which, alone or in any combination, may comprise patentable subject matter.

One embodiment of the system for monitoring person position in a person support apparatus comprises a person support apparatus comprising a lower frame and a variably elevatable upper frame with respect to the lower frame and at least one side rail defining the lateral extremity of said person support apparatus. At least one image capture device is coupled to the person support apparatus. A processor configured to communicate with the image capture device, the processor configured to detect facial features from the communication, and a timer in communication with the processor. The timer is configured to reset to a predetermined value upon receiving a command from the processor indicating motion of a person supported by a person support apparatus has exceeded a predetermined threshold, as determined by the processor upon processing the communication from the image capture device.

One embodiment of the system for monitoring person position in a person support apparatus comprises at least one image capture device, a processor in communication with the image capture device, the processor configured to detect facial features from the communication, and a timer in communication with the processor. The timer is configured to reset to a predetermined value upon receiving a command from the processor indicating motion of a person supported by a person support apparatus has exceeded a predetermined threshold, as determined by the processor upon processing the communication from the image capture device.

One embodiment of the method for monitoring person position in a person support apparatus comprises capturing a first image and determining if a person is in a first position, capturing a second image if a person is not in the first position, and determining if a person is in a second position. The method further comprises capturing a third image if a person is not in the second position and determining if a person is in a third position.

Another embodiment of the method for monitoring person position in a person support apparatus comprises capturing an image, determining at least one facial feature from the image, determining motion of the at least one facial feature over a predetermined period of time and triggering an alarm if the motion over the predetermined period of time is less than a predetermined threshold.

Another embodiment of the system for monitoring person position in a person support apparatus comprises at least one image capture device and a processor in communication with the image capture device. The processor is configured to detect facial features from the communication. The processor comprises a timer configured to reset to a predetermined value indicating motion of a person supported by a person support apparatus has exceeded a predetermined threshold, as determined by the processor, upon processing the communication from the at least one image capture device.

BRIEF DESCRIPTION OF DRAWINGS

The accompanying drawings incorporated in and forming a part of the specification illustrate several aspects of the claimed subject matter and, together with the description, serve to explain the principles of the claimed subject matter. In the drawings:

DETAILED DESCRIPTION OF ILLUSTRATIVE EMBODIMENTS

The embodiments of the claimed subject mater and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be briefly mentioned or omitted so as to not unnecessarily obscure the embodiments of the claimed subject matter described. The examples used herein are intended merely to facilitate an understanding of some ways in which the claimed subject matter may be practiced and to further enable those of skill in the art to practice various embodiments of the claimed subject matter described herein. Accordingly, the examples and embodiments herein are merely illustrative and should not be construed as limiting the scope of the claimed subject matter, which is defined solely by the appended claims and applicable law. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein with respect to embodiments is used for the purpose of describing particular embodiments only, and is not intended to limit the scope of the claimed subject matter.

Unless defined otherwise, all technical and scientific terms used herein have the same meanings as commonly understood by one of ordinary skill in the art.

Figure 1:
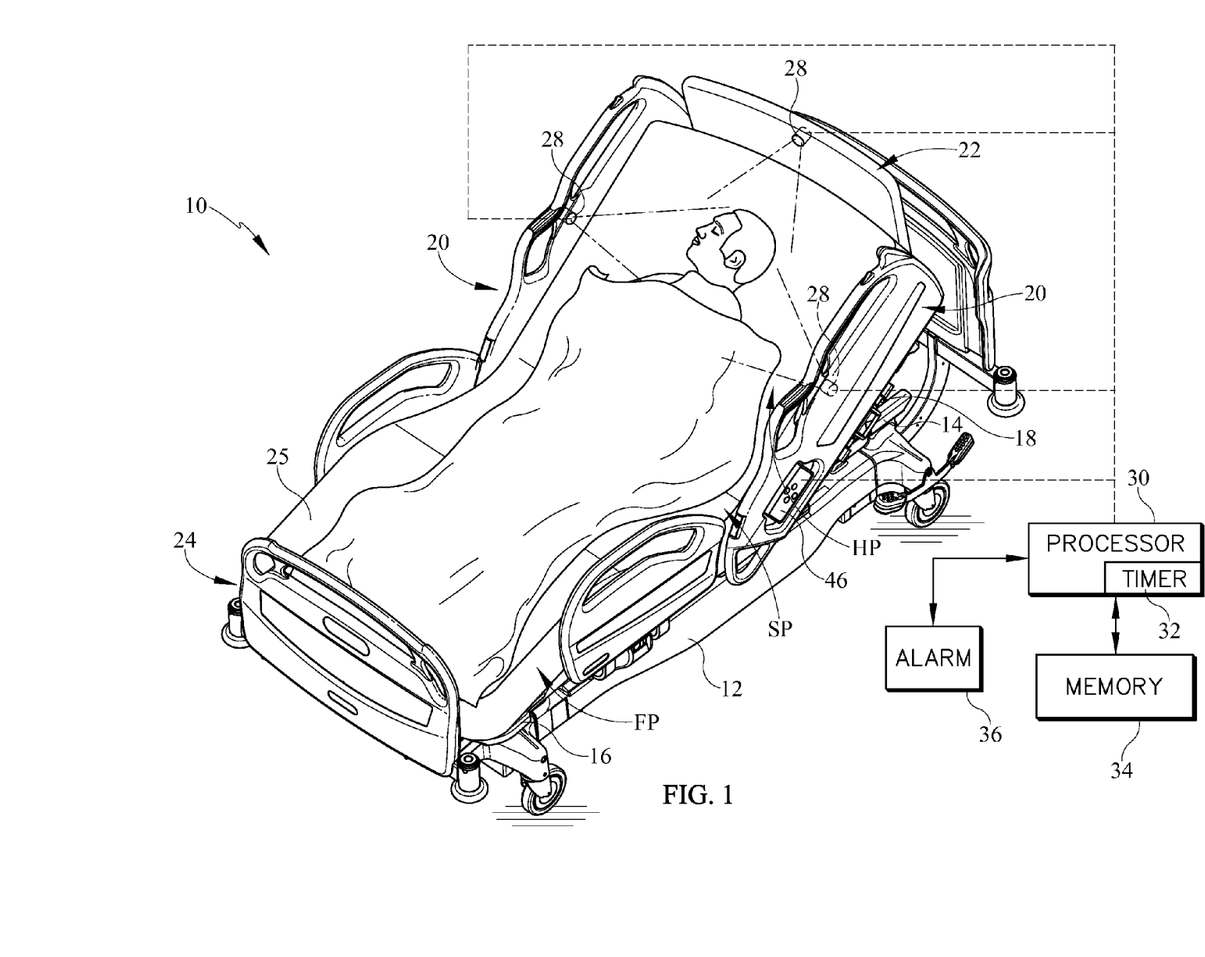
FIG. 1 is a perspective view of one embodiment of a person support apparatus comprising a system for monitoring person position, constructed according to one or more of the principles disclosed herein.

A system for monitoring person position in a person support apparatus according to one illustrative embodiment of the current disclosure is shown in FIG. 1. In the illustrative embodiment shown in FIG. 1, the person support apparatus 10 is a hospital bed. The person support apparatus 10 includes a lower frame or base 12, a plurality of supports 18 coupled with the lower frame 12, and an upper frame 14 supported on the plurality of supports 18 above the lower frame 12. The upper frame 14 is configured to variably elevate with respect to the lower frame 12. The person-support apparatus 10 includes a deck 16 supported on the upper frame 14. The deck 16 of the person-support apparatus 10 includes a head support section HP supporting head of the person, a seat support section SP and a foot support section FP supporting feet of the person. The deck 16 further supports a person support surface or a mattress 25 as shown in FIG. 1, the mattress 25 may be of foam construction and/or may comprise air bladders. The person support apparatus 10 may be a stretcher or an operating table in another embodiment. The deck 16 comprises a section configured to pivot with respect to the lower frame 12. The person support apparatus 10 also comprises siderails which define the lateral extremities of the persona support apparatus. Siderails are configured to actuate between at least two positions, an upper deployed position and a lower stowed position. In the upper deployed position the top extreme of the siderails is higher than the person support surface 25. FIG. 1 shows a system for monitoring person position in a person support apparatus comprising at least one image capture device 28 embedded in the side rail 20. Additionally, an image capturing device is positioned in the head board 22. The image capture device 28 is configured to capturing images in any electromagnetic frequency range, including the infra-red spectrum and the visible spectrum. In one embodiment, the image capture device 28 is configured to capture images in wavelength range of 380 nanometers to 740 nanometers with a frequency range of 405 Terahertz to 790 Terahertz. In the illustrative embodiment shown in FIG. 1, an image capture device 28 is mounted on a side rail 20 on each side of the person support apparatus 10. In addition, an image capture device 28 is mounted on the head board 22. In another embodiment, an image capture device 28 may be mounted on the foot board 24. A processor 30 is in communication with at least one image capture device 28 and receives images taken by the devices. The processor 30 can be any device configured to receive at least one input signal and in one embodiment have the capability to provide at least one output signal. Several types of processors are well known, including but not limited to programmable or preprogrammed types. The processor 30 receives signals from the at least one image capture device 28 and processes the signals to determine the presence and orientation of facial features. A multitude of techniques may be used to determine the presence and orientation of facial features, including but not limited to boundary recognition, feature recognition, Eigen face recognition techniques, Fisher face recognition techniques and feature-based graph recognition techniques. In this embodiment at least one facial feature, including but not limited to the position of eye lids, position of eyes, position of nose, position of lips and position of at least one ear can be determined. In one embodiment, the position of the eye lids is used to determine whether the patient is asleep. A timer 32 is configured to reset to a predetermined value when a change in patient position in excess of a predetermined threshold is detected by the processor. The timer 32 as shown in FIG. 1 functions based on the processor 30 clock in one embodiment. In another embodiment, the timer 32 is a separate device in communication with the processor and which resets to a predetermined value upon getting a signal from the processor 30. The timer 32 may be a counter and/or a routine based indirectly on time, calculated by running a cyclical chain of operations in one embodiment. Therefore, the timer 32 is configured to determine the length of time a patient is in any one position and resets when the patient changes position. The processor 30 is in communication with a Graphical User Interface (GUI) 46 to display alarms and other messages. The GUI 46 is integral to the person support apparatus 10 in one embodiment and is used to control other functions of the person support apparatus 10. The GUI 46 also allows for user inputs and commands including, but not limited to set thresholds for the time duration for lack of patient motion, sensitivity of determination of patient motion and value to which the timer 32 may be reset to, up on patient motion being detected. These thresholds may be in the form of an upper bound (should not exceed), lower bound (should exceed) and/or a range. The processor 30 is in communication with an alarm 36 and if patient motion does not exceed a predetermined threshold for a predetermined time duration, the processor 30 triggers alarm 36. In one embodiment, the processor 30 triggers alarm 36 if the motion of patient's eye lids relative to at least one other facial feature does not exceed a predetermined threshold for a predetermined time duration, indicating that the patient may be asleep for longer than desired or may be unconscious. A memory 34 in communication with the processor 30 is configured to store the time duration elapsed since the motion of the patient exceeded a predetermined threshold. The memory 34 in another embodiment stores historical data of patient motion, including the time duration and the sequence of motion. In this embodiment, the memory 34 stores the historical data of alarms and messages generated by the processor and/or the user inputs from the GUI 46. The memory 34 may be of any type, including volatile and non-volatile types.

Figure 2:
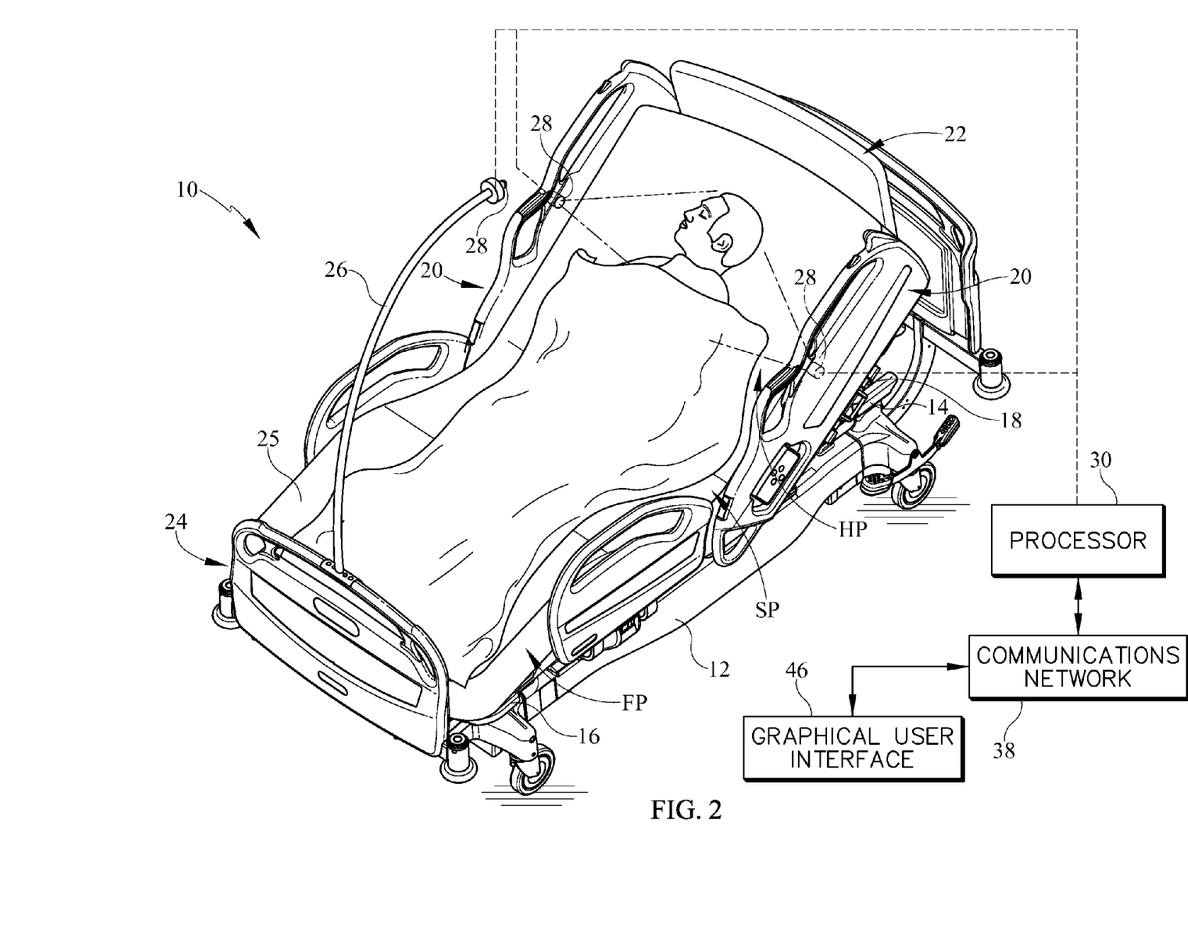
FIG. 2 is a perspective view of another one embodiment of a person support apparatus comprising a system for monitoring person position, constructed according to one or more of the principles disclosed herein.

Another system for monitoring person position in a person support apparatus according to another illustrative embodiment of the current disclosure is shown in FIG. 2. As shown in FIG. 2 at least one image capture device 28 is mounted on a side rail 20 on each side of the person support apparatus 10. Although the figure shows image capture devices 30 mounted to side rails adjacent to the head support section HP, the image capture devices 28 may be mounted to any other side rail in another embodiment. A camera support boom 26 is connected to the foot board 24 and supports an image capture device 28. In another embodiment, multiple camera support booms may be utilized and connected to any one of side rails 20, head board 22 or any other portion of the person support apparatus 10. In yet another embodiment, the camera support boom 26 may be an independent structure supported by the floor, ceiling or another piece of furniture. A processor 30 is in communication with the at least one image capture device 28. The processor 30 is also in communication with a communication network 38. The communication network 38 may be of any type, including but not limited to Wide Area Network (WAN), Local Area Network (LAN), Virtual Private Network (VPN), telephone lines, optical communications, internet communications or telex. In this embodiment, a Graphical User Interface (GUI) 46 is connected to the processor 30 via the communication network 38 and configured to display alarms and other messages. The GUI 46 allows for user inputs and commands including, but not limited to set thresholds for the time duration for lack of patient motion, sensitivity of determination of patient motion and value to which a timer may be reset to up on patient motion being detected. In this embodiment the system for monitoring person position has a dedicated GUI 46. These thresholds can be in the form of an upper bound (should not exceed), lower bound (should exceed) and/or a range. In one embodiment, the processor 30 receives signals from the at least one image capture device 28 and transmits the signals via the communication network 38 to a remote data processing station where signals are processed to determine the presence and orientation of facial features. The duration of activity and/or lack thereof would also be determined at the remote data processing station. Alarms, messages and historical including, but not limited to those previously described are stored in and transmitted from the remote data processing. In another embodiment, the processor 30 receives signals from the at least one image capture device 28 and processes the signals to determine the presence and orientation of facial features, while communicating a time stamp up on detecting patient motion over a predetermined threshold and/or other alarms described herein.

Figure 3:
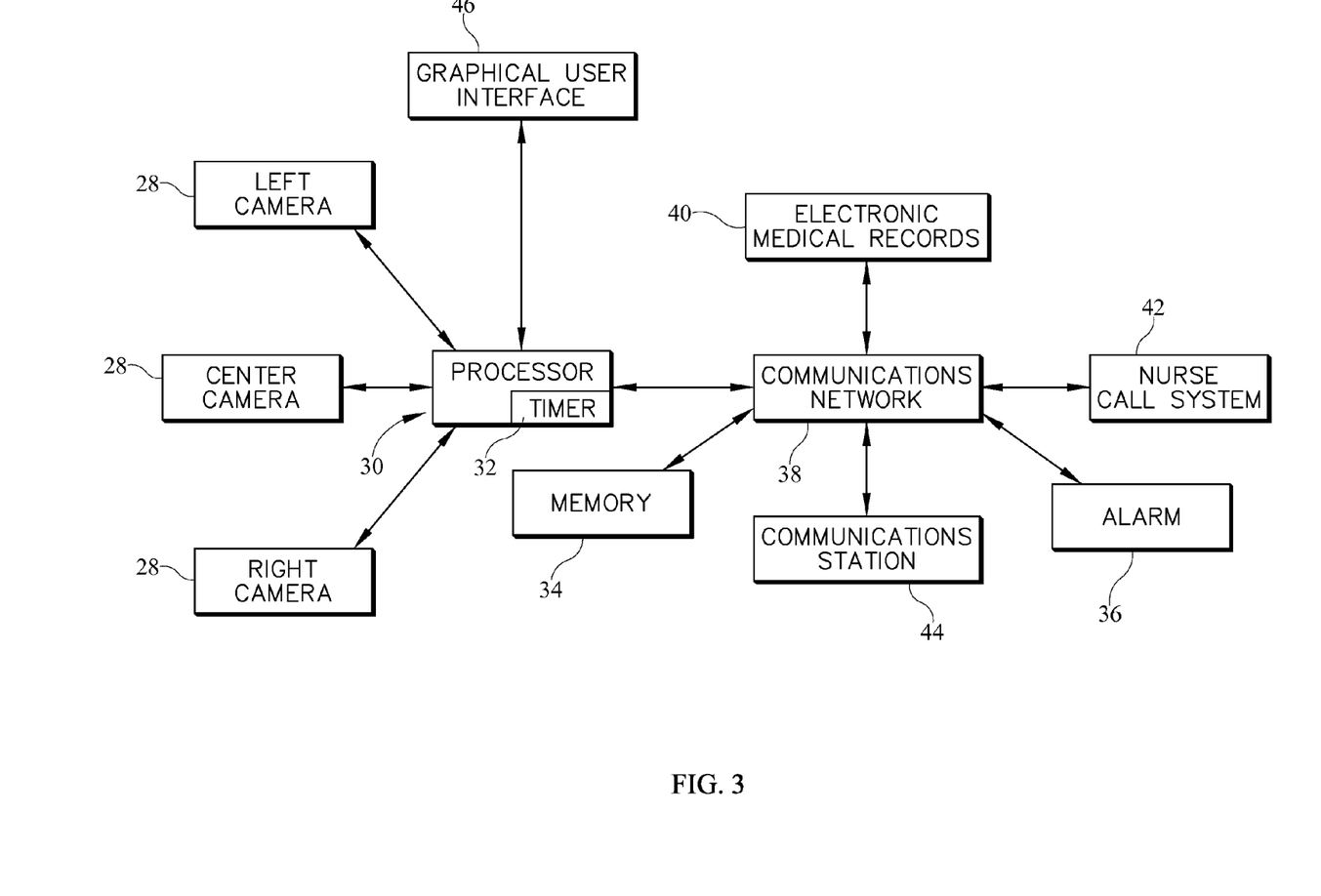
FIG. 3 is a block diagram of yet another one embodiment of a person support apparatus comprising a system for monitoring person position, constructed according to one or more of the principles disclosed herein.

FIG. 3 shows a block diagram of one embodiment of a system for monitoring person position in a person support apparatus according to one illustrative embodiment of the current disclosure. Three image capture devices 28 (left, center and right) are in communication with a processor 30, although in other embodiments, any number of image capture devices 28 may be used. The image capture devices 28 are configured to capturing images in any electromagnetic frequency range, including the infra-red spectrum and the visible spectrum. A processor 30 is in communication with at least one image capture device 28 and receives images taken by the devices. The processor 30 can be any device configured to receive at least one input signal and having the capability to provide at least one output signal. Several types of processors are well known, including but not limited to programmable or preprogrammed types. The processor 30 receives signals from the at least one image capture device 28 and processes the signals to determine the presence and orientation of facial features. A multitude of techniques may be used to determine the presence and orientation of facial features, including but not limited to boundary recognition, feature recognition, Eigen face recognition techniques, Fisher face recognition techniques and feature-based graph recognition techniques. In this embodiment, the processor 30 processes the signals to determine any one or combination of facial features, including the position of eye lids, position of eyes, position of nose, position of lips and position of at least one ear. In this embodiment, the position of the eye lids is used to determine whether the patient is asleep. Timer 32 is configured to reset to a predetermined value when a change in patient position in excess of a predetermined threshold is detected by the processor. The timer 32 as shown in FIG. 3 functions based on the processor 30 clock in one embodiment. In another embodiment, the timer 32 is a separate device in communication with the processor and which resets to a predetermined value upon getting a signal from the processor 30. Therefore, the timer 32 is configured to determine the length of time a patient is in any one position and resets when the patient changes position. In the embodiment of FIG. 3, the processor 30 is in communication with a Graphical User Interface (GUI) 46 to display alarms and other messages. The GUI 46 is integral to the person support apparatus 10 in this embodiment and is used to control other functions of the person support apparatus 10. The GUI 46 also allows for user inputs and commands including, but not limited to set thresholds for the time duration for lack of patient motion, sensitivity of determination of patient motion and value to which the timer 32 may be reset to up on patient motion being detected. These thresholds can be in the form of an upper bound (should not exceed), lower bound (should exceed) and/or a range. The processor 30 is also in communication with a communication network 38. The communication network 38 may be of any type, including but not limited to Wide Area Network (WAN), Local Area Network (LAN), Virtual Private Network (VPN), telephone lines, optical communications, internet communications or telex. The communication network 38 is in communication with at least one Electronic Medical Record (EMR) 40 or another healthcare information database, a hospital communication station 44 and a nurse call system 42. The communication station 40 is a centralized location wherein one or more patients may be monitored by a caregiver. In one embodiment the communication station 44 may be stationary, while in another embodiment, it may be a mobile unit to accommodate prompt deployment.

Figure 4A:
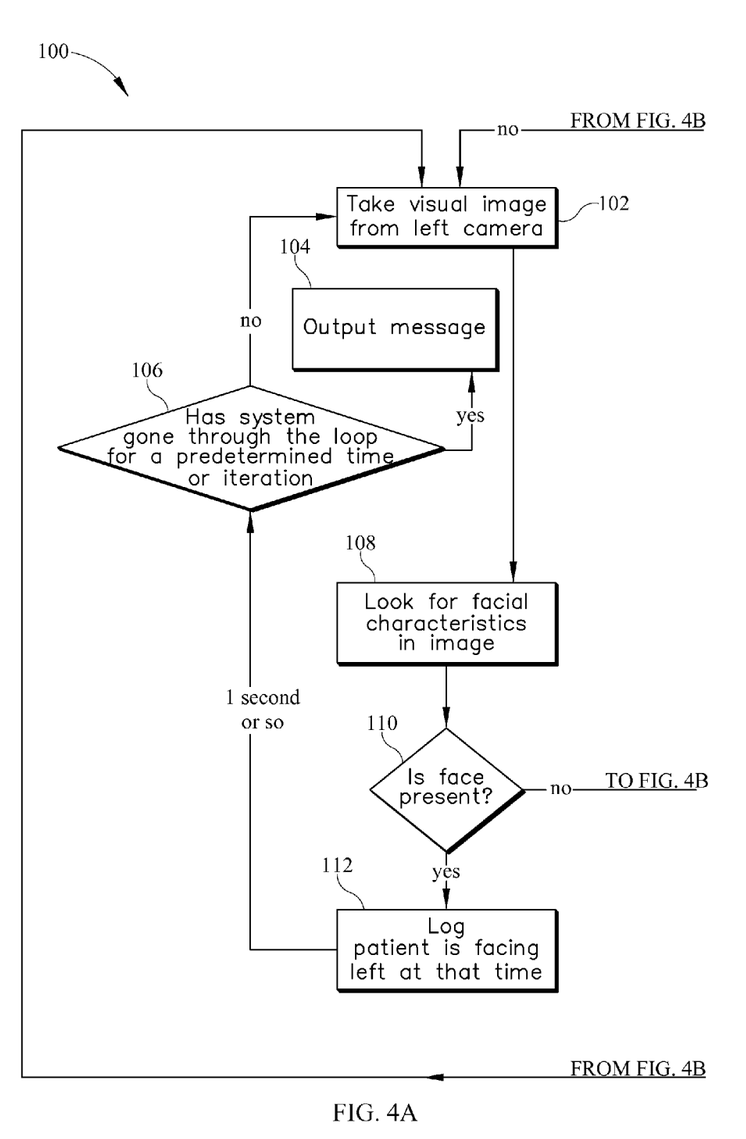
FIG. 4A, FIG. 4B and FIG. 4C are flow diagrams describing an algorithm of a system for monitoring person position in a person support apparatus, constructed according to one or more of the principles disclosed herein.
Figure 4B:
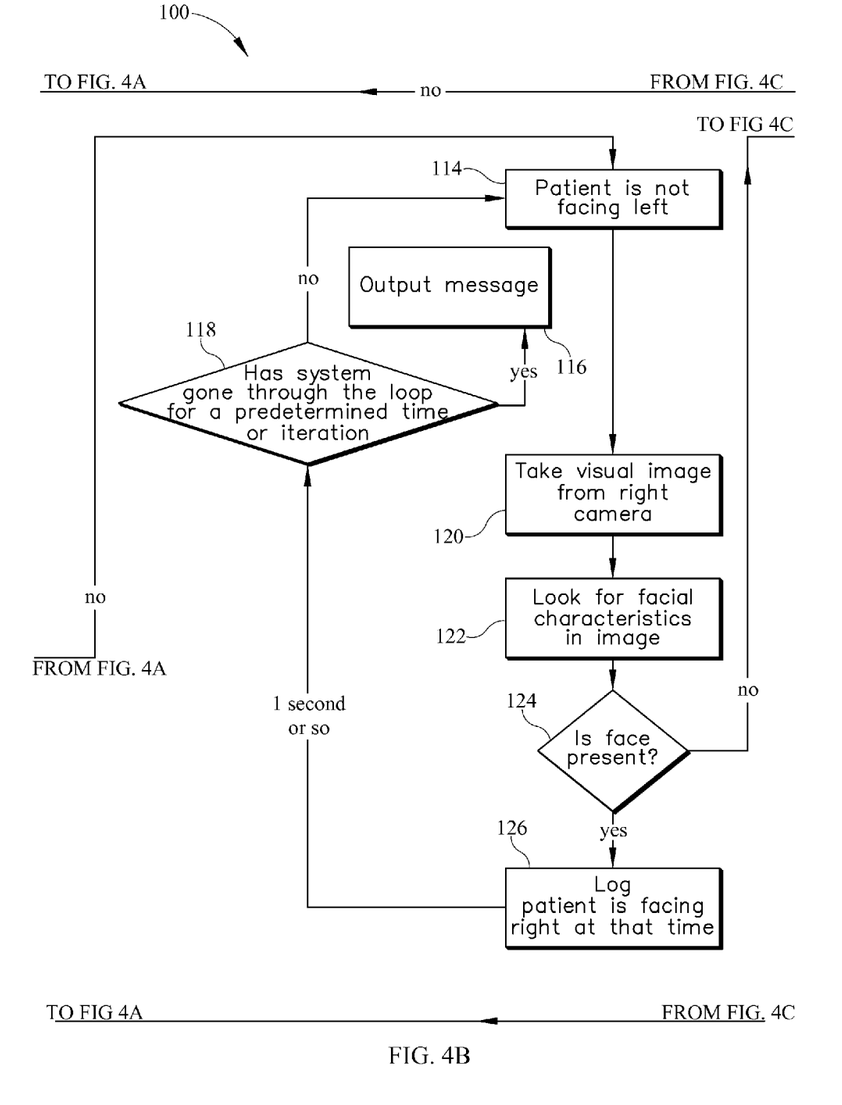
Figure 4C:
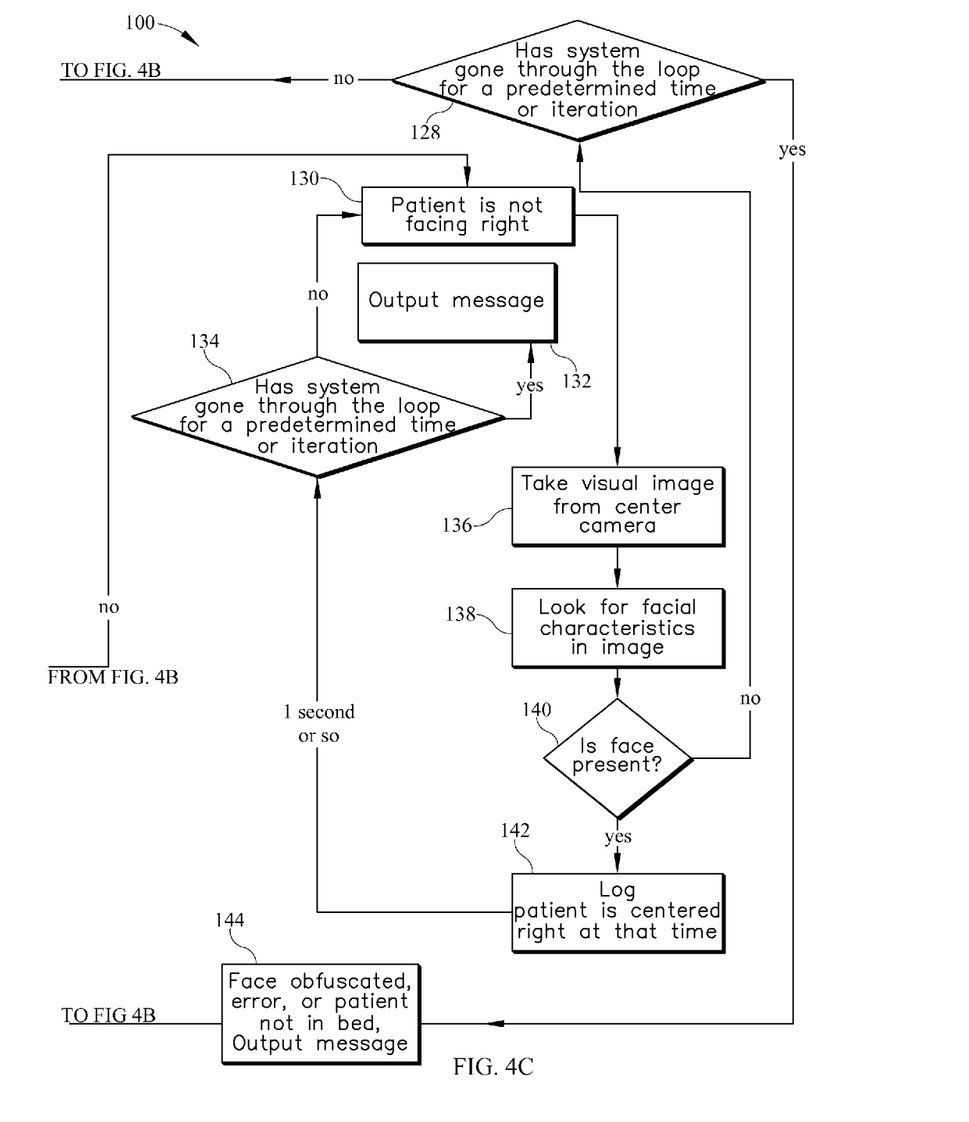

The algorithm shown in FIG. 4A, FIG. 4B & FIG. 4C describes one embodiment of the method for monitoring person position 100 in a person support apparatus. As shown in FIG. 4A, during operation 102 an image capture device positioned generally to the left of the patient supported by the person support apparatus takes at least one image. The image is then processed during operation 108 to identify facial characteristics in the at least one image. A determination is made during operation 110 as to whether a face is present in the at least one image and if it is determined that a face is present, during operation 112 the time at which this determination is made is logged. A determination is made during operation 106 as to whether the system has gone through this loop for greater than a predetermined time period or a number of iterations with respect to a predetermined threshold. Operation 106 helps determine whether the patient has been in a position where in their face is generally oriented towards the left image capture device for a period greater than a predetermined time period. In one embodiment the threshold is so selected as to identify movement of specific facial features, such as the eyelids remaining closed for duration greater than a predetermined threshold. The threshold may also be adjusted to accommodate motion of the patient while their face is generally oriented towards the left image capture device and/or lack thereof. If in operation 106 it is determined that the system has gone through the loop for a predetermined time or number of iterations, a message is output during operation 104. This message may be in the form of activation of an audio and/or visual alarm, display of message on the GUI 46 and/or transmittal over communication network 38. On the other hand if during operation 106 it is determined that the system has not gone through the loop for a predetermined time or number of iterations, another image is taken by the image capture device during operation 102. If during operation 110 it is determined that a face is not present in the image taken, a determination is made that the patient in not facing left during operation 114 shown in FIG. 4B.

As described in FIG. 4B, in operation 120 an image capture device positioned generally to the right of the person supported by the person support apparatus takes at least one image. The image is then processed during operation 122 to identify facial characteristics in the at least one image. A determination in made during operation 124 as to whether a face is present in the at least one image and if it is determined that a face is present, during operation 126 the time at which this determination is made is logged. A determination is then made during operation 118 as to whether the system has gone through this loop for greater than a predetermined time period or larger number of iterations than a predetermined threshold. Operation 118 determines whether the patient has been in a position where in their face is generally oriented towards the right image capture device for a period greater than a predetermined threshold. In one embodiment the threshold may be so selected as to identify movement of specific facial features, such as the eyelids remaining closed for duration greater than a predetermined threshold. The threshold may also be adjusted to accommodate motion of the patient while their face is generally oriented towards the right image capture device and/or lack thereof. If in operation 118 it is determined that the system has gone through the loop for a predetermined time or number of iterations, a message is output during operation 116. This message may be in the form of activation of an audio and/or visual alarm, display of message on the GUI 46 and/or transmittal over communication network 38. On the other hand if during operation 118 it is determined that the system has not gone through the loop for a predetermined time or number of iterations, another image is taken by the image capture device during operation 120. During operation 124 if it is determined that a face is not present in the image taken, a determination is made that the patient in not facing right during operation 130 shown in FIG. 4C.

As shown in FIG. 4C, in operation 136 an image capture device positioned generally to capture a plan view/view from the top of the person support apparatus takes at least one image. The image is then processed during operation 138 to identify facial characteristics in the at least one image. A determination in made during operation 140 as to whether a face is present in the at least one image and if it is determined that a face is present, during operation 142 the time at which this determination is made is logged. A determination is then made during operation 134 as to whether the system has gone through this loop for greater than a predetermined time period or larger number of iterations than a predetermined threshold. Operation 134 determines whether the patient has been in a position where in their face is generally oriented upwards towards ceiling and therefore the center image capture device for a period greater than a predetermined threshold. In one embodiment the threshold may be so selected as to identify movement of specific facial features, such as the eyelids remaining closed for duration greater than a predetermined threshold. The threshold may also be adjusted to accommodate motion of the patient while their face is generally oriented towards the right image capture device and/or lack thereof. If in operation 134 it is determined that the system has gone through the loop for a predetermined time or number of iterations, a message is output during operation 132. This message may be in the form of activation of an audio and/or visual alarm, display of message on the GUI 46 and/or transmittal over communication network 38. On the other hand if during operation 134 it is determined that the system has not gone through the loop for a predetermined time or number of iterations, another image is taken by the image capture device during operation 136. During operation 140 if it is determined that a face is not present in the image taken, a determination is then made during operation 128 as to whether the system has gone through this loop of toggling between the left, right and center image capture devices for greater than a predetermined time period or larger number of iterations than a predetermined threshold. If in operation 128 it is determined that the system has gone through the loop of toggling between the left, right and center image capture devices for a predetermined time or number of iterations, a determination is made the face is obfuscated or the patient is not in bed and a message is output during operation 144. This message may be in the form of activation of an audio and/or visual alarm, display of message on the GUI 46 and/or transmittal over communication network 38. On the other hand if during operation 128 it is determined that the system has not gone through the loop for a predetermined time or number of iterations, another image is taken by the left image capture device during operation 102 as shown in FIG. 4A.

As will be appreciated by one of skill in the art, the various aspects of the present invention may be embodied as a method, system, or computer program product. Moreover, the various aspects of the present invention may take the form of an entirely hardware embodiment or an embodiment combining software and hardware aspects.

The present subject matter is described with reference to schematics, flowchart illustrations and/or block diagrams of methods and apparatus systems according to embodiments of the invention. It will be understood that each block of the flowchart illustrations and/or block diagrams, and combinations of blocks in the flowchart illustrations and/or block diagrams may also be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. The equations in the specification and the flowcharts and block diagrams in the Figures illustrate the architecture, functionality, and operation of possible implementations of systems, methods and computer program products according to various embodiments of the present invention. In this regard, each equation or block in the flowchart or block diagrams may represent a module, segment, or portion of code, which comprises one or more executable instructions for implementing the specified logical function(s). It should also be noted that, in some alternative implementations, the functions might occur out of the order as presented herein. For example, two blocks shown in succession may, in fact, be executed substantially concurrently, or the blocks may sometimes be executed in the reverse order, depending upon the functionality involved. It will also be noted that each equation in the specification, and each block of the block diagrams and/or flowchart illustration, and combinations of blocks in the block diagrams and/or flowchart illustration, can be implemented by special purpose hardware-based systems that per form the specified functions or acts, or combinations of special purpose hardware and computer instructions.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

We claim:

1. A system for monitoring a person, comprising:
   a person support apparatus;
   a first image capture device arranged to capture an image in a first direction;
   a second image capture device arranged to capture an image in a second direction which differs from the first direction;
   a processor including instructions operable to cause the processor to process the captured images to carry out facial recognition on the captured images;
   a timer configured to communicate with the processor to track a time period or a number of iterations; and
   an alarm configured to be triggered by the processor;
   wherein the processor determines if a face has been present in an image captured by the first image capture device, and if the processor determines that the face is present in the image captured by the first image capture device, the timer tracks the time period or the number of iterations;
   if the processor determines a face is not present in the image captured by the first image capture device, the system acquires an image from the second image capture device to determine if a face has been present in an image captured by the second image capture device, and if the processor determines that the face is present in the image captured by the second image capture device, the timer tracks the time period or the number of iterations;
   wherein the processor triggers the alarm when the time period or the number of iterations is greater than a predetermined threshold; and
   wherein the timer resets the time period or the number of iterations resets to a predetermined value upon receiving a command from the processor indicating that movement of a person supported by a person support apparatus has exceeded the predetermined threshold, as determined by the processor upon processing the communication from at least one of the image capture devices.

2. The system of claim 1 further comprising a memory device configured to communicate with said processor, said memory device configured to store at least one value of said predetermined threshold.

3. The system of claim 1 further comprising a graphical user interface configured to communicate with said processor, said graphical user interface configured to allow user input to establish said predetermined threshold.

4. The system of claim 3, said graphical user interface configured to display a message indicating person position.

5. The system of claim 1 further comprising a communication network configured to communicate with said processor.

6. The system of claim 5 further comprising at least one electronic medical record configured to communicate with said communication network.

7. The system of claim 5 further comprising a nurse call system configured to communicate with said communication network.

8. The system of claim 5 further comprising a communication station configured to communicate with said communication network.

9. The system of claim 5 further comprising an alarm configured to communicate with said communication network.

10. The system of claim 1 wherein the image capture devices are mounted on the person support apparatus.

11. The system of claim 1 wherein said processor controls at least one function of a person support apparatus.

12. The system of claim 1 wherein the system outputs the message only if the determination that a face has been present in an image captured by the first image capture device for greater than a predetermined time period or for a number of iterations greater than a predetermined threshold is accompanied by a determination that the person has also been substantially motionless for a period of time.

13. The system of claim 1, wherein the system further outputs a first indication that the person is not present or the person's face is obfuscated, if a face is not present in the at least one of the images captured by one of the image capture devices for a number of iterations greater than a first predetermined iteration threshold.

14. The system of claim 1, wherein the system further outputs a second indication that the person is inactive if a face is present in the image from a specific one of the image capture devices for a number of iterations greater than a second predetermined iteration threshold, which need not be equal to the first predetermined iteration threshold.

15. The system of claim 14 wherein the system outputs the second indication only if the image from the specific one of the image capture devices also indicates that the person has been substantially motionless for a predetermined period of time or predetermined number of iterations.

16. The system of claim 1, wherein the system further outputs a first indication that the person is not present or the person's face is obfuscated, if a face is not present in the at least one of the images captured by one of the image capture devices for a time greater than a first predetermined time threshold.

17. The system of claim 1, wherein the system further outputs a second indication that the person is inactive if a face is present in the image from a specific one of the image capture devices for a time greater than a second predetermined time threshold which need not be equal to the first predetermined time threshold.

18. The system of claim 17 wherein the system outputs the second indication only if the image from the specific one of the image capture devices also indicates that the person has been substantially motionless for a predetermined period of time or predetermined number of iterations.

19. A method of monitoring a person's position in a hospital bed comprising:
    setting a timer to a predetermined value, the timer configured to track a time period or a number of iterations;
    determining, from a first image captured from a first image capture device, if a person's face is in a first position; and
    if the person's face is not in the first position determining, from a second image captured from a second image capture device, if the person's face is in a second position; and if the person's face is not in the second position determining, from a third image captured from a third image captured device, if the person's face is in a third position; and if the person's face is not in the third position and if the determinations from the first, second and third images have each been made at least once, reaching a conclusion about person status;

tracking, subsequent to determining that the person's face is in one of the first, second, and third positions, the time period or the number of iterations;

resetting the timer to the predetermined value if the person's face is no longer detected in a previously detected position; and triggering an alarm if the timer reaches the predetermined value indicating that the person's face remained in one of the first, second, and third positions for the predetermined time period or the number of iterations.

20. The method of claim 19 wherein said determination if the a person's face is in said first position is made by searching for at least one facial feature in said first image.

21. The method of claim 20 wherein said at least one facial feature comprises at least one of position of eyes, position of eyelids, position of nose, position of at least one ear, position of nose and position of at least one lip.

22. The method of claim 19 further comprising the operation of logging the position of the person's face over time.

23. The method of claim 19 further comprising the operation of triggering an alarm if the person's face is not in said third position.

24. The method of claim 19 wherein the first, second and third images are discrete images.

25. The method of claim 19 wherein the first, second and third images are captured from different directions.

26. The method of claim 19 wherein capturing the first, second and third images comprise capturing images of a person occupying the hospital bed.

27. The method of claim 19 wherein:

in the event that determining if the person's face is in the first position, determining if the person's face is in the second position, and determining if the person's face is in the third position have not each been carried out for greater than a predetermined time period or larger number of iterations than a predetermined threshold, repeating at least is in the first position.

28. The method of claim 27 wherein:

in the event that determining if the person's face is in the first position, determining if the person's face is in the second position, and determining if the person's face is in the third position have been carried out for greater than a predetermined time period or larger number of iterations than a predetermined threshold, outputting a message.

29. The method of claim 19 wherein the person support apparatus includes left and right siderails, the first image capture device is a first camera mounted on the left siderail and the second image capture device is a second camera mounted on the right siderail.

30. The method of claim 19 wherein the conclusion is that the person is present in the bed and the person's face is obfuscated.

31. The method of claim 19 wherein the conclusion is that the person is not present in the bed.

* * * * *